United States Patent [19]

Lee

[11] 4,289,623

[45] Sep. 15, 1981

[54] HOLLOW FIBER DIALYSIS

[75] Inventor: Kyu H. Lee, King of Prussia, Pa.

[73] Assignee: Extracorporeal Medical Specialties, Inc., King of Prussia, Pa.

[21] Appl. No.: 843,502

[22] Filed: Oct. 19, 1977

Related U.S. Application Data

[63] Continuation of Ser. No. 629,082, Nov. 5, 1975, abandoned.

[51] Int. Cl.³ .................................. B01D 31/00
[52] U.S. Cl. ............................ 210/247; 210/321.3; 210/433.2; 210/456
[58] Field of Search ............ 210/321 A, 321 B, 321 R, 210/433 M, 247, 456; 55/158; 422/48

[56] References Cited

U.S. PATENT DOCUMENTS

| | | | |
|---|---|---|---|
| 2,715,097 | 8/1955 | Guarino | 210/321 B |
| 3,728,256 | 4/1973 | Cooper | 210/321 B X |
| 3,831,763 | 8/1974 | Breysse et al. | 210/433 M X |
| 4,001,110 | 1/1977 | Geen et al. | 210/22 A |
| 4,031,012 | 6/1977 | Gics | 210/321 A |
| 4,038,190 | 7/1977 | Baudet et al. | 210/321 A X |

FOREIGN PATENT DOCUMENTS

| | | | |
|---|---|---|---|
| 2444540 | 3/1975 | Fed. Rep. of Germany | 210/321 B |
| 2514763 | 10/1975 | Fed. Rep. of Germany | 210/321 A |

*Primary Examiner*—Charles N. Hart
*Assistant Examiner*—David R. Sadowski

[57] ABSTRACT

Improved dialyzer construction has elongated tubular casing with enlarged casing ends and longitudinally-extending partitioning that divides its interior into a plurality of generally parallel passageways containing hollow dialysis fibers, the casing ends containing dialyzate flow manifolding and directing means for receiving dialyzate from a supply thereof, directing it from one casing end to the other through one of the passageways around the fibers, and so to and fro through the successive passageways, finally directing the dialyzate out through a discharge opening. The dialyzate flow can in each fiber-containing passageway be counter-current to the flow within the fibers of the liquid being dialyzed. A gas by-pass can be provided in the partitioning at one end to bleed out gas that tends to accumulate at the high point of the to-and-fro dialyzate travel.

22 Claims, 16 Drawing Figures

HOLLOW FIBER DIALYSIS

This application is a continuation of application Ser. No. 629,082 filed Nov. 5, 1975, now abandoned.

The present invention relates to dialysis, particularly dialysis of liquids such as blood.

There have been many suggestions for improving dialysis equipment especially of the artificial kidney type. A great many so-called coil-type artificial kidneys are in use in which the dialysis element is a tube many inches in diameter, but flattened and spirally wound with a spacer to separate the turns of the winding. An artificial kidney so made is relatively large in size, and there have been suggestions for smaller constructions having bundles of thousands of hollow fibers each a very narrow tube that functions as a dialysis element, but this modified construction still presents problems. An example of hollow fiber apparatus is shown in U.S. Pat. No. 3,442, 002, and a fiber which has recently come into use for hollow fiber dialyzers is the deacetylated cellulose acetate fiber referred to in U.S. Pat. No. 3,546,209. These fibers are generally required to be kept wet with water at all times after the de-acetylation, in order to maintain their dialytic permeability. This has led to the awkwardness of shipping and storing dialyzers based on such hollow fibers, while the fibers are filled with water and with the water containing formaldehyde to keep it from developing microbial growth. Before each use it then becomes necessary to flush out all the formaldehyde.

Among the objects of the present invention is the provision of improved hollow fiber dialyzer constructions.

The foregoing as well as additional objects of the present invention are more fully explained in the following descriptions of several of its exemplifications, reference being made to the accompanying drawings in which:

A feature of the present invention is the provision of a hollow fiber dialyzer having an elongated tubular casing with ends of larger bore than its central portion, the central portion containing longitudinally-extending partitioning that divides its interior into a plurality of generally parallel passageways, the casing ends containing dialyzate flow manifolding and directing means for receiving dialyzate from a supply thereof, directing it from one casing end to the other through one of the passageways, and so to and fro through the successive passageways, finally directing the dialyzate out through a discharge opening, bundles of parallel hollow dialysis fibers being crowded into at least all of the passageways in which the directing means directs dialyzate flow in the same direction.

The following examples illustrate very desirable manners of preparing hollow fiber dialyzers in accordance with the present application.

EXAMPLE 1

Figures 1, 2, 3, 4:
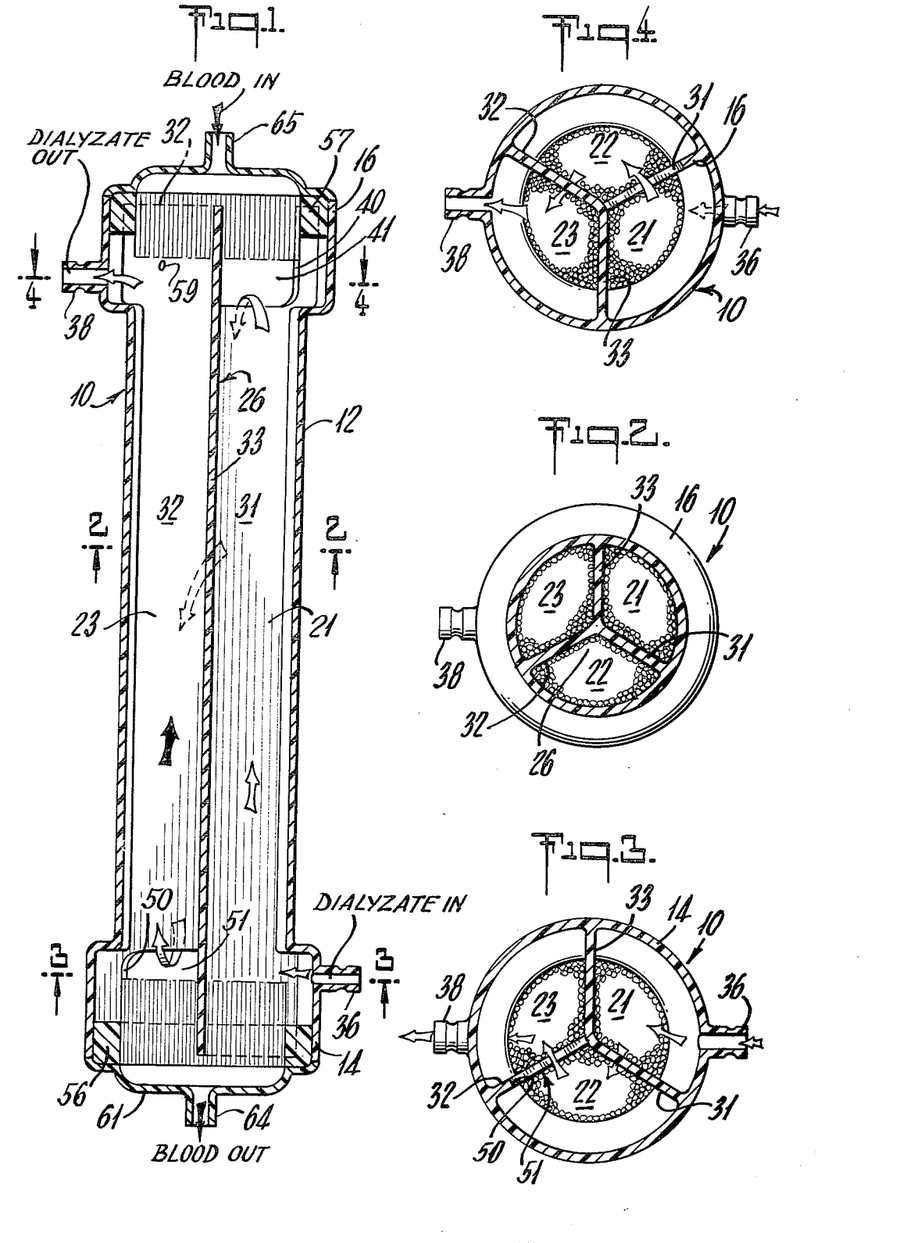
FIG. 1 is an elevational view partly in section and partly broken away, of a hollow fiber dialyzer in accordance with the present invention.
FIGS. 2, 3 and 4 are sectional views of the construction of FIG. 1, taken along the lines 2—2, 3—3 and 4—4, respectively.

A dialysis casing such as shown at 10 in FIG. 1 and molded or cemented together from polycarbonate or polystyrene resin, is first provided. This casing has an over-all length of about 7½ inches with its intermediate portion 12 having an internal diameter of 1⅜ inches, each end 14, 16 being of enlarged bore having internal diameters about 1½ inches. The tubular length of the interior of the casing is divided into three individual passageways 21, 22, 23 by an axial web 26 of three flanges, 31, 32 and 33. An inlet tube 36 opens into enlarged end 14, and a discharge tube 38 leads out from end 16.

Web 26 has flow control means at each end 14, 16 arranged so that fluid entering inlet 36 flows upwardly through passageway 21 from end 14 to end 16, then at end 16 moves from the top of passageway 21 to the top of passageway 22, then downwardly through passageway 22 to lower end 14 where it then transfers to the bottom of passageway 23 along which it moves upwardly to end 16 for discharge through outlet 38. To effect this flow control, flange 31 is arranged as a barrier seal against the outer wall of the casing throughout the length of lower end 14 as well as throughout the length of the intermediate portion 12, but not at the upper end 16. Instead at that upper end flange 31 is cut out as shown at 40 to provide a flow-through space 41 that thus opens between the upper ends of passageways 21 and 22.

Flange 32 is similarly shaped in an opposite sense so that at its lower portion it provides an edge 50 spaced from the lowest point of casing end 14 to provide a flow-through space 51 between the lower ends of passageways 22 and 23.

A batch of hollow cuprammonium regenerated cellulose fibers having a wall thickness of about 12 microns plus or minus 2 microns and an internal diameter of about 200 microns plus or minus 50 microns is unspooled, preferably from a plurality of spools in parallel strands, cut to a length of about 9 inches and carefully cleaned. As generally supplied these fibers are made be extruding cuprammonium cellulose solution through an annular die into a regenerating bath while introducing a water-immiscible liquid into the bore of the hollow extrudate. A typical water-insoluble liquid is isopropylmyristate. After regeneration is completed careful washing with isopropanol removes such liquid. The interiors of the fibers can then be wet with a softening agent such as glycerine, preferably leaving about 5% of the softening agent by weight of the clean fiber. This softening is not essential but helps guard the fibers against breakage or damage during subsequent handling, and does not detract from the effectiveness by which the fibers are sealed into the casing 10.

A bundle of two to three thousand fibers so prepared is then inserted into one of the passageways 21, 22, 23, and additional bundles in each of the remaining passageways. This insertion can be expedited by first sliding over the bundle a tapered sleeve of polyethylene, then introducing the filled sleeve, narrow end first, into one of the passageways, and finally pulling the sleeve off the introduced bundle. At the narrow end of the taper the fibers are arranged to project from the sleeve so they can be gripped to help pull the sleeve off the other ends of the fibers.

When all the passageways are filled with fibers, the potting can be started. At each end of the casing each bundle of fibers projects a short distance. Each of these projecting ends is dipped in melted carnauba wax which is then permitted to solidify after the carnauba wax has peenetrated a very short distance into all of the individual fibers. The casing is then clamped longitudinally between potting heads connected to a potting compound container as illustrated in FIG. 19 of U.S. Pat. No. 3,442,002, and centrifuged as also indicated in that patent while the uncured liquid freshly mixed potting mixture is poured into the potting compound container. This mixture can be a polyurethane prepolymer resin with a chain extender, or an epoxy cement mixture as described in U.S. Pat. No. 3,442,002, or a hardenable polysiloxane liquid or other settable resin.

When a hardenable polysiloxane liquid with a curing agent such as chlorplatinic acid is used, the centrifuging is conducted at about 350 g while the mixture is heated, and after about ½ hour at 150° F. the potting mixture is cured to the point that it no longer flows. The potting heads are then unclamped and removed, and the curing completed by holding the dialyzer in an air oven at 150° F. for two hours. After that the potting mixture is a cleanly cutting solid and a sharp metal blade is used to cut the potting mixture flush with the open ends 14, 16 of the casing. This leaves the construction as illustrated in FIG. 1, the potting composition being shown at 56 and 57. Covers 61, 62 each equipped with a flow connection 64, 65 are then fitted to the casing ends 14, 16 as by welding or cementing, although they can also be be threaded in place if desired. The construction is then complete and only needs a flushing through to remove the water-soluble softening agent from the inside of the hollow fibers before it is placed in service. The dialyzers can be stored either before or after washing out the softening agent, without significantly affecting its dialysis properties.

When the dialyzer is used it is generally held with end 16 up, a source of dialyzate is connected to inlet 36, discharge 38 is connected to waste, and a supply of blood to be dialyzed connected to inlet 65 with a blood return to outlet 64. In use bubbles of air or other gases can form in the dialyzate and tend to rise toward the upper end 16 of the dialyzer. To keep those bubbles from becoming trapped at the upper ends of passageways 21 and 22 and collecting there in an amount that could interfere with the dialysis, a small bleed 59 is shown as provided at the upper end of web flange 32. For a flange with a wall thickness of 1/16 inch a round opening as little as ½ millimeter in diameter will enable the gas trapped at the above-mentioned ends to readily make its way into the upper end of passageway 23 and out through discharge opening 38, without significantly reducing the effectiveness of the dialysis. The gas vent can even be made slightly smaller as for example 0.3 mm. in diameter. The optimum width of the vent is related to the thickness of the wall through which it penetrates. For wall thicknesses greater than 1/16 inch the vent width is preferably a little larger than ½ millimeter.

A feature of the dialyzer construction of FIG. 1 is that such dialyzers are readily manufactured with more uniform dialysis effectiveness than corresponding dialyzers in which there is no partitioning and web 26 is completely omitted. Notwithstanding the enlarged ends 14, 16 which serve as dialyzate manifolds that bring the dialyzate into direct contact with the outer layers of fibers in the fiber bundles, the dialyzate has a tendency to make its way through one end of the dialyzer to the other through the easiest path and thus find and establish a channel, even when the fibers are fairly well packed in place. Such channeling greatly reduces the effectiveness of the dialysis particularly through the walls of those fibers that are some distance laterally spaced from the channel. When this happens with a dialyzer containing only a single dialyzate passageway, its efficiency becomes so poor that it generally has to be discarded.

Such channeling is more likely to take place as the wall thickness of the hollow fibers diminishes and as the fiber diameter decreases; these cause the fibers to be more flexible so that it is easier for the dialyzate to create a channel by deflecting the fibers. Wall thicknesses of about 5 to about 20 microns are suitable for effective use and thicknesses of from about 10 to about 15 microns are preferred. Fibers with internal passageways not over about 500 microns wide, preferably ranging from about 100 to about 300 microns in width, are very effective. Cuprammonium regenerated hollow fibers of this type are relatively stiff, particularly when dry, and are accordingly very easy to handle in the assembling of a bundle for insertion in a dialyzer, and in the insertion itself.

In the construction of FIG. 1 a channeling-induced drop in efficiency of passageway 21 can also occur, but when that happens the dialyzate emerging from passageway 21 is less loaded with contaminants so that it becomes more effective in its subsequent passage through passageways 22 and 23.

In addition each of the passageways 21, 22 and 23 is narrower than it would be without the web 26, and channeling becomes less likely in narrower passageways. Also the total length of fibers contacted by the dialyzate in the construction of FIG. 1 is three times the length contacted if web 26 were omitted, and the efficiency loss through channeling diminishes as such length increases.

Because of the more reproducible greater efficiencies of the construction of FIG. 1, dialyzers having an operating length between potting seals 56, 57, of only about 15 centimeters can be readily manufactured with the desired high qualities. This small bulk is particularly desirable, although in general overall lengths of from about 6 to about 12 inches can be attractive for hospital use.

EXAMPLE 2

FIGS. 5, 6, 7 and 8 illustrate a modified dialyzer 110 pursuant to the present invention. In this dialyzer there are three parallel dialyzer passageways along the lines of FIG. 1 but the flow of dialyzate is arranged so that throughout its fiber-contacting path it moves on the outside of the individual fibers in a direction countercurrent to the flow of blood or other medium being dialyzed within the fibers.

Figure 5:
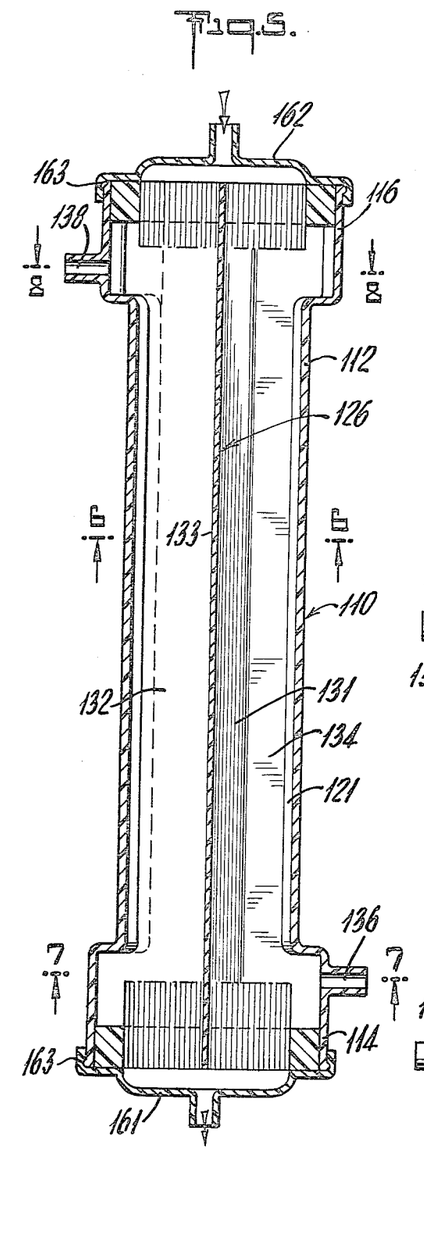
FIG. 5 is a view similar to FIG. 1 of a modified hollow fiber dialyzer representative of the present invention.
Figure 6:
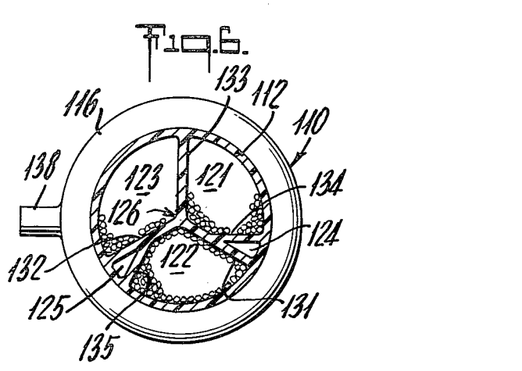
FIGS. 6, 7 and 8 are sectional views of the construction of FIG. 5 taken along the lines 6—6, 7—7 and 8—8, respectively.
Figure 7:
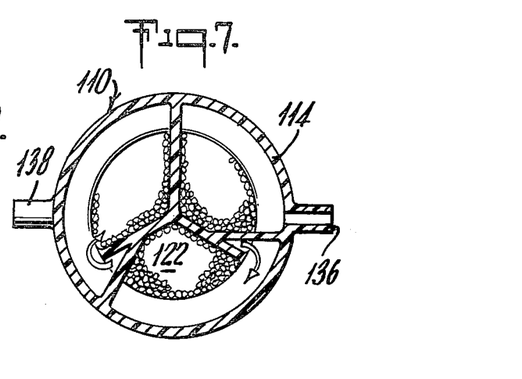
Figure 8:
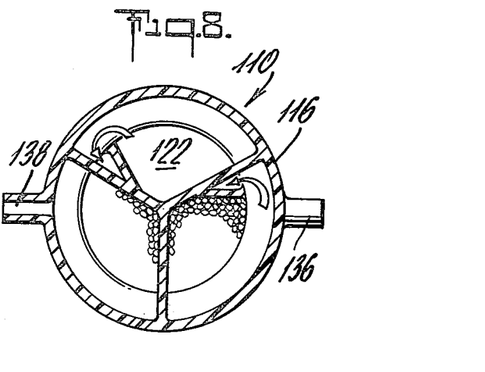

As in the construction of FIG. 1, dialyzer 110 has a central tubular section 112 with enlarged ends 114, 116 and with a partitioning web 126 inserted or molded in section 112. Web 126 has flanges 131, 132, 133 similar to the three flanges of web 26, and in addition also has two supplemental flanges 134, 135 that define supplemental passageways 124, 125.

The bundles of hollow fibers are contained in passageways 121, 122, 123; passageways 124, 125 being unfilled so that they provide paths for the dialyzate to flow while out of contact with the fibers.

The flow of dialyzate is controlled by appropriate shaping of the web flanges in the construction of FIG. 5 so that it enters and flows upwardly first through passage 121 then downwardly through passage 124 then back upwardly through passageway 122 returning this time to the bottom via passageway 125, and finally completing the dialysis by an upward travel through passageway 123 and discharge at outlet 138. For this result, the upper ends of webs 134 and 135 are spaced from the inside wall of casing end 116 and the lower ends of webs 131 and 132 are spaced from the inside surface of casing end 114, as more clearly illustrated in FIGS. 7 and 8.

No gas vent is provided in the construction of FIG. 5 inasmuch as the dialyzate flow rate is fairly high in the very narrow return passageways 124, 125. Thus a flow rate of only about one foot a second is generally sufficient to sweep out gas bubbles that tend to form. For slower flow rates, as for example when the dialyzate is discarded after a single passage through the dialyzer and is not recirculated from outlet 138 back to inlet 136, gas venting can be provided in the construction of FIG. 5.

Gas venting can be eliminated where the dialyzate is treated to reduce gas evolution, as for example by boiling it under reduced pressure before it is introduced into the dialyzer. This removes almost all of the dissolved gases, and the maintenance of some pressure on the dialyzate as it is impelled through the dialyzer acts as an additional preventive to gas evolution.

The dialyzer casings of the present invention need not be circular in cross-section but can be oval, rectangular or triangular if desired, both in their external shape as well as in the shape of the passageways. Similarly, they do not have to be perfectly linear in longitudinal direction.

EXAMPLE 3

FIGS. 9 through 13 illustrate a dialyzer 210 according to the present invention which is generally triangular in cross-section, particularly at its ends 214, 216. Those ends each have a mounting rib 217 which helps in positioning end connector covers 262. Moreover each rib 217 can be provided with a ridge 219 which need only be about 15 to about 20 mils high that helps in welding the cover in place as by sonic or ultrasonic vibration of the mounted cover against that ridge. Upon vibration in this manner the ridge and the ridge-engaging portion of the cover fuse as a result of the frictional heating effects of the vibration between them, and weld together making a very effective fluid-tight seal.

The construction and operation of FIGS. 9 through 13 generally corresponds to that of FIGS. 5 through 8, and similar portions such as partitioning web 226, passageways 221, 222 and 223 for receiving the hollow fibers, passageways 224 and 225 for dialyzate return, and inter-passage spacings 241, are similarly numbered. However, to better seal the blood or other dialyzand away from undesired crevices and the like, covers 262 are each provided with an internal sealing lip 263 shaped to engage the potting seal 257 outside the fiber-containing zone. The dialyzand is thus kept from penetrating into the crevice 265 between the internal surface of the cover and external surface of the casing wall.

Figures 9, 10, 11, 12, 13:
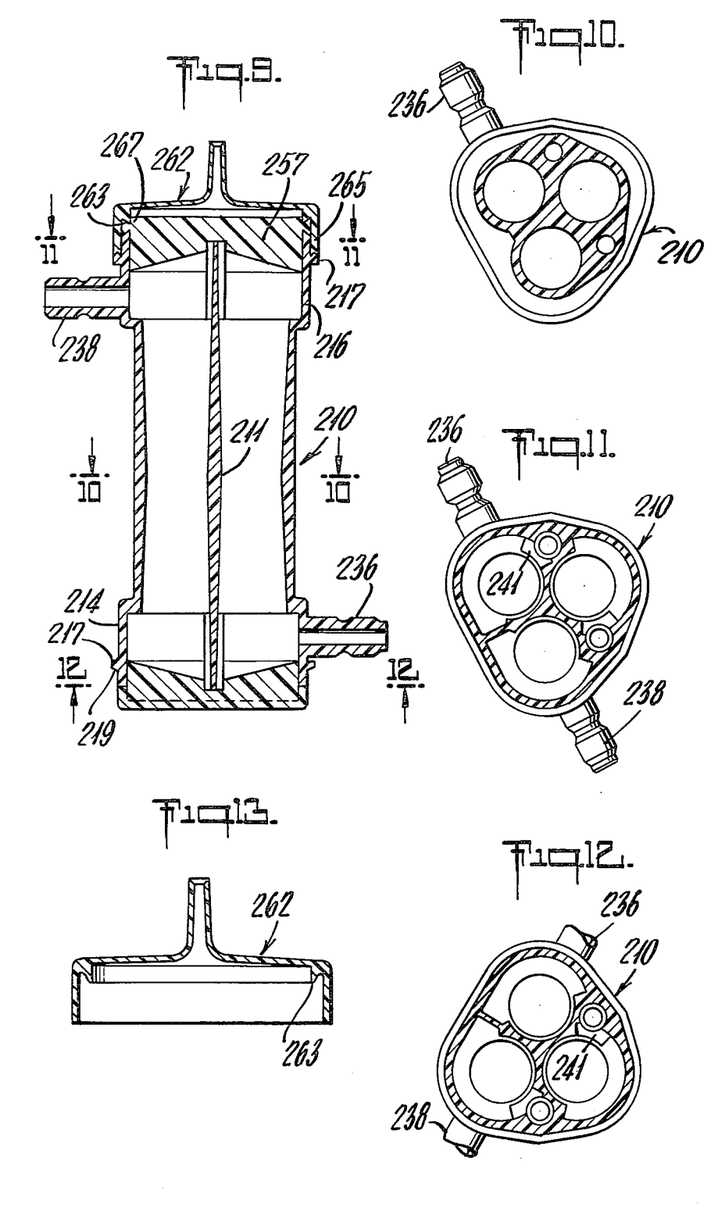
FIGS. 9, 10, 11 and 12 are views similar to FIGS. 1, 2, 3 and 4 of a further modified dialyzer typical of the present invention.
FIG. 13 is a sectional view of a cap suitable for use with the construction of FIG. 9.

To further help with such sealing, the potting seal 257 can be arranged to project out a short distance 267, such as ⅛ inch, beyond the casing end.

EXAMPLE 4

Figure 14:
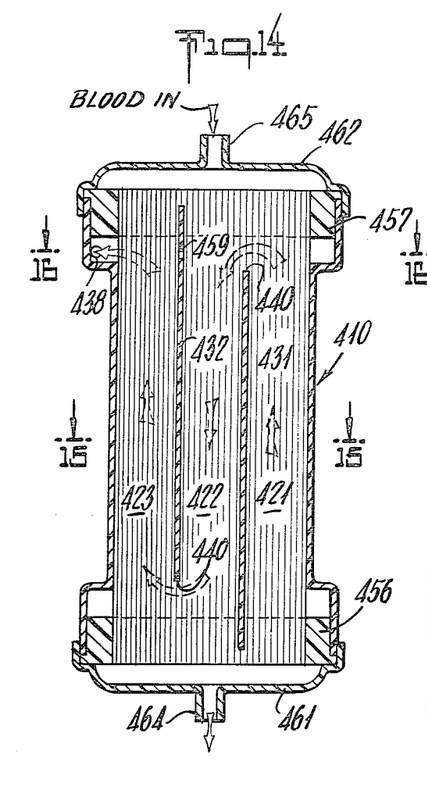
FIGS. 14, 15 and 16 are views similar to FIGS. 1, 2 and 3 of yet another embodiment of the present invention.
Figure 15:
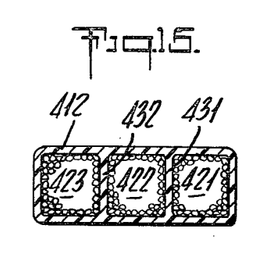
Figure 16:
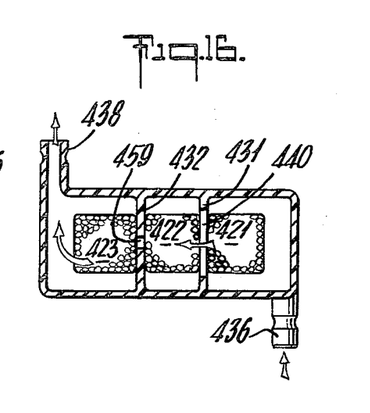

FIGS. 14, 15 and 16 illustrate a dialyzer 412 having a generally rectangular configuration both in its external aspect as well as in its passageways. Such a configuration makes better use of space and can contain more fibers than other configurations having the same overall dimensions.

The construction and operation of this exemplification, as well as the numbering of its parts, is similar to that of FIGS. 1 through 4, except that its covers 462 and cover engagement are like those of FIGS. 9 through 13 without the internal sealing lip. Internal sealing is provided in FIG. 14 by having its end covers 462 tightly engage the outer margin of the potting seal. Also instead of having the fiber-containing passageways 421, 422 and 423 arrayed generally circumferentially around casing 410, these passageways are arranged in a simple row all lying in what can be considered the same thick plane.

The fiber bundles can be inserted in the dialyzer passageways without the help of a sleeve, particularly if the walls of a casing end provide a gradual taper from their large internal bore down to the smaller bore of central portion 12 or 112. Alternatively the bundles can be sleeved and the sleeves left in the dialyzer in position around the bundles. This alternative is particularly desirable when the sleeves are of relatively thin wall section, i.e. about 3 mils, so that they do not occupy much room.

The insertion of the fiber bundles is also made easier if this is done when the casings are hot. The heat expands the casing and thus provides a little more room for more readily sliding the bundles into place, after which the casing cools down and tightly encloses the fibers, thus making for added efficiency. Instead of an elongated sleeve to help the fiber insertion, a single narrow length of plastic or even wire can be looped around a fiber bundle adjacent one end, and tied or crimped against the fibers so as to provide a tail for the bundle. The bundle can then be pulled through a passageway by first passing the tail through the passageway and then pulling on the tail.

It is generally desirable to clean the hollow fibers for the dialysis as by washing or rinsing them with a readily volatilizable solvent, particularly where the bores in the fibers contain a liquid which should not contact the dialyzand or dialyzate.

The advantages of partitioning are obtained when the dialyzer is partitioned to provide only two parallel dialyzing passageways. A very simple construction of this type has inlet and outlet tubes 36, 38 on opposite sides of the upper casing 16 with a single central web extending longitudinally the entire length of the casing but with an opening in its lower portion.

The partitioning can even be more subdivided than is shown in the drawings so as to provide 4 or 5 parallel dialysis passageways, but the use of more partitions takes away some of the space for fibers so that the bulk of the casing has to be increased to maintain the dialyzing effectiveness.

The partitioning of the present invention simplifies the mechanical handling in the manufacture of the dialyzer. The reduced width of the individual passageways, e.g. one to three centimeters, as compared to an unpartitioned dialyzer, reduces the number of fibers per passageway and thus simplifies the preparation of the individual bundles. By way of illustration, the task of preparing a 6000-fiber bundle for an unpartitioned dialyzer is more complex than that of preparing three 2000-fiber bundles for use in the dialyzer of FIG. 1 or FIG. 5 or FIG. 9.

The fiber-containing passageways can also be double tapered as illustrated at 211 in FIG. 9 so that they provide a constriction in their central portions. Such a constriction of about ½ to 1 millimeter helps grip the fibers and keep them from being deflected by the flow around them, thus reducing the tendency to channelling.

Another feature of the present invention is that the different compartments of the described dialyzers need not be used for the same function. One of the compartments can for example be used to hold an absorbent such as activated charcoal or the like, instead of fibers, so as to absorb impurities or other undesirable ingredients in the dialyzand. Different kinds of fibers can be used in different passageways to obtain different dialysis effects on the dialyzand as it passes through the dialyzer. Indeed some of the passageways, such as passageway 124, can be filled with absorbent for the purpose of treating the dialyzate as it moves through the dialyzer and better condition the dialyzate for its passage through the remaining fiber-containing passageways.

The potting of the fiber ends can be accomplished with techniques other than that described above. Thus the preliminary dip of the fibers to plug their bores can be into melted resin-modified waxes or thermoplastic resins or compositions that harden to form thermosetting resins. The potting mixture itself can for example be used as a preliminary dip of shallow depth, followed by deeper potting. Also, by maintaining slightly higher pressure in unplugged fiber bores as against the pressure over the potting mixture into which the unplugged fiber ends are dipped, the potting mixture is kept at a low level within those bores and the preliminary dip to plug those bores can alternatively be sealed by melting the fiber ends when they are of fusible nature, and in this way make a prior dip unnecessary.

While centrifugal force applied to the liquid potting mixture helps assure that such mixture thoroughly impregnates all crevices and pores around and between the fibers and in this way assures thorough sealing of the dialyzate chamber from the dialyzand, gas pressure applied over the liquid potting composition during the potting, has a similar effect. One end of a fiber bundle can accordingly be potted at a time, without the need for the centrifugal potting apparatus.

Also the covers 61, 62 can be arranged to snap on over the potted ends of the dialyzer, as shown in FIG. 5 at 161, 162 for example. Such covers can be relatively flexible and the potted ends they snap over can be fitted with ridges as at 163 to help lock the snap-on covers in place.

The dialysis discussed above is to be distinguished from osmosis in that the dialysis uses fibers whose walls are extremely porous, much too porous for use in osmosis. This comparison is more clearly shown by the fact that a reverse osmosis process desalinating brackish water for instance, requires membranes of relatively non-porous material such as polyvinyl chloride, as well as the use of a driving pressure greater than the osmotic pressure and as high as practicable. An attempt to carry out such a reverse osmosis with the cuprammonium regenerated cellulose as described above, will merely cause the brackish water to rapidly filter through the regenerated cellulose fibers and emerge at the discharge face of the cellulose in substantially the same condition as it entered the entrance face.

The dialyzer construction of the present invention can also be used with the dialyzate passing through the bores of the hollow fibers and the dialyzand moving along the outside of the fibers, although this arrangement is not desirable where blood is the dialyzand. However with osmosis-type fibers, the structural arrangement of the present invention is suitable for osmotic processes such as reverse osmosis, and in such use it is preferred to pass the fluid being treated around the hollow fibers so that the high pressures used on such fluids in reverse osmosis is applied to the exteriors of the fibers. Fiber failures are then not likely to cause leakage.

The apparatus of the present invention is also suitable for use in gas separation, again with an appropriate type of fiber, or in gas treatment of liquids as in the oxygenation of blood where silicone fibers are preferred.

Obviously many modifications and variations of the present invention are possible in the light of the above teachings. It is, therefore, to be understood that within the scope of the appended claims the invention may be practiced otherwise than as specifically described.

What is claimed:

1. A hollow fiber dialyzer having an elongated tubular casing containing partitioning that divides its interior into a plurality of separate longitudinally-extending passageways, dialyzate flow directing means for receiving dialyzate from an external source and directing it to flow from one casing end to the other through one of the passageways and then back to said one casing end through another of the passageways and so to and fro lengthwise through the other passageways and finally out of the casing, at least two of the passageways each having a longitudinally-extending bundle of elongated hollow blood dialysis fibers extending lengthwise through it, and means connected to deliver blood to be dialyzed from an inlet to the fiber ends of each of such bundles at the same end of the casing and to receive the blood from the other ends of the hollow fibers for delivery to an outlet, characterized in that only some but not all of the passageways have said bundles of fibers and the remaining passageways do not contain dialysis fibers, and the dialyzate flow directing means directs dialyzate to flow from one casing end to the other in alternating fashion through the passageways having bundles of fibers and the passageways which do not contain fibers so that the dialyzate flow through each of the passageways having bundles of fibers is always in the same lengthwise direction.

2. A hollow fiber dialyzer as in claim 1 wherein the passageways having said bundles of fibers have a relatively larger cross-section than the cross-section of the passageways which do not contain dialysis fibers.

3. A hollow fiber dialyzer as in claim 2 wherein the lengthwise direction of dialyzate flow through the relatively larger cross-section passageways having said bundles of fibers is opposite to the direction of blood flow through the hollow fibers from the blood inlet to the blood outlet.

4. A hollow fiber dialyzer as in claim 1 wherein said casing has a substantially rectangular cross-section.

5. A hollow fiber dialyzer as in claim 1 wherein said plurality of separate longitudinally-extending passageways have a substantially rectangular cross-section.

6. A hollow fiber dialyzer as in claim 1 wherein said casing has a substantially rectangular cross-section and said plurality of separate longitudinally-extending passageways have a substantially rectangular cross-section.

7. A hollow fiber dialyzer having an elongated tubular casing containing partitioning that divides its interior into at least three separate longitudinally-extending passageways, dialyzate flow directing means for receiving dialyzate from an external source and directing it to flow from one casing end to the other through one of the passageways and then back to said one casing end through another of the passageways and so to and fro lengthwise through the other passageways and finally out of the casing, at least two of the passageways each having a longitudinally-extending bundle of elongated hollow blood dialysis fibers extending lengthwise therethrough, at least one of the passageways not containing dialysis fibers, and means connected to deliver blood to be dialyzed from an inlet to the fiber ends of each of such bundles at the same end of the casing and to receive the blood from the other ends of the hollow fibers for delivery to an outlet, characterized in that the passageways having said bundles of fibers have a relatively larger cross-section than the cross-section of the passageways which do not contain dialysis fibers, and the said at least one passageway which does not contain dialysis fibers has a cross-section which is circular and which also is sufficiently narrow to cause the flowing dialyzate to sweep out gas bubbles that may form in the dialyzate.

8. A hollow fiber dialyzer as in claim 7 wherein the passageways having said bundles of fibers are generally circular in cross-section throughout their length between the dialyzate entrance and exit ends.

9. A hollow fiber dialyzer as in claim 7 wherein there are two passageways having said bundles of fibers and one passageway which does not contain dialysis fibers.

10. A hollow fiber dialyzer as in claim 7 wherein there are three passageways having said bundles of fibers and two passageways which do not contain dialysis fibers.

11. A hollow fiber dialyzer as in claim 7 wherein the number of passageways which do not contain dialysis fibers is one less than the number of passageways having said bundles of fibers.

12. A hollow fiber dialyzer having an elongated tubular casing containing partitioning that divides its interior into at least five separate longitudinally-extending passageways, dialyzate flow directing means for receiving dialyzate from an external source and directing it to flow from one casing end to the other through one of the passageways and then back to said one casing end through another of the passageways and so to and fro lengthwise through the other passageways and finally out of the casing, at least three of the passageways each having a longitudinally-extending bundle of elongated hollow blood dialysis fibers extending lengthwise therethrough, and means connected to deliver blood to be dialyzed from an inlet to the fiber ends of each of such bundles at the same end of the casing and to receive the blood from the other ends of the hollow fibers for delivery to an outlet, characterized in that there are at least two passageways which do not contain dialysis fibers, and the said at least three passageways having bundles of fibers are arranged in closely-packed triangular relationship.

13. A hollow fiber dialyzer as in claim 12 wherein the said at least two passageways which do not contain dialysis fibers are smaller in cross-section than those passageways having said bundles of fibers and said at least two passageways of smaller cross-section are located adjacent the lateral periphery of the elongated casing, and the casing is molded of a transparent material.

14. A hollow fiber dialyzer as in claim 12 wherein the said at least two passageways which do not contain dialysis fibers are smaller in cross-section than those passageways which contain dialysis fibers and are located adjacent the lateral periphery of the elongated casing, and the casing is molded of a resin selected from the group consisting of polystyrene and polycarbonate.

15. A hollow fiber dialyzer as in claim 12 wherein there are three passageways having said bundles of fibers and two passageways which do not contain dialysis fibers.

16. A hollow fiber dialyzer as in claim 15 wherein said two passageways which do not contain dialysis fibers are smaller in cross-section than said three passageways having said bundles of fibers and are located adjacent the lateral periphery of the elongated casing.

17. A hollow fiber dialyzer having an elongated tubular casing containing partitioning that divides its interior into a plurality of separate longitudinally-extending passageways, dialyzate flow directing means for receiving dialyzate from an external source and directing it to flow from one casing end to the other through one of the passageways and then back to said one casing end through another of the passageways and so to and fro lengthwise through the other passageways and finally out of the casing, at least two of the passageways each having a longitudinally-extending bundle of elongated hollow blood dialysis fibers extending lengthwise therethrough, and means connected to deliver blood to be dialyzed from an inlet to the fiber ends of each of said bundles at the same end of the casing and to receive the blood from the other ends of the hollow fibers for delivery to an outlet, characterized in that at one end of the casing the flow directing means contains a gas by-pass connected between successive passageways to permit gas bubbles trapped at that end, when the dialyzer is operated with that end up, to be discharged out of the casing without having to be carried by the dialyzate to the other end.

18. A tubular casing integrally molded to contain longitudinal partitioning that subdivides it into five longitudinally extending side-by-side passageways, three of them being of much wider cross-section than the other two, the three wider passageways being about equal in size, the partitioning containing inter-passage communication openings that permit fluid introduced into one of the wider passageways near one end of the casing to move through that passageway to a location near the other end of the casing, then move from there into one of the smaller passageways and back through that smaller passageway to a location near said one end, from there move into a second wider passageway and through that passageway to a location near said other end, from there into the second smaller passageway and through that passageway back to a location near said one end, from there into the third wider passageway and through that passageway to a location near said other end, characterized in that the casing is about 6 to about 12 inches long, and in that the five passageways are clustered about a common longitudinal centerline with the three wider passageways arranged in closely-packed triangular relationship, and the two smaller passageways are each circular in cross-section.

19. A hollow fiber dialyzer having an elongated tubular casing containing partitioning that divides its interior into at least five separate longitudinally-extending passageways, dialyzate flow directing means for receiving dialyzate from an external source and directing it to flow from one casing end to the other through one of the passageways and then back to said one casing end through another of the passageways and so to and fro lengthwise through the other passageways and finally out of the casing, at least three of the passageways each having a longitudinally-extending bundle of elongated hollow blood dialysis fibers extending lengthwise therethrough, at least two of the passageways not containing dialysis fibers, and means connected to deliver blood to be dialyzed from an inlet to the fiber ends of each of said bundles at the same end of the casing and to receive the blood from the other ends of the hollow fibers for delivery to an outlet, characterized in that the passageways having said bundles of fibers are generally circular in cross-section throughout their length between the dialyzate entrance and exit ends and are clustered around a common centerline, and the passageways which do not contain dialysis fibers are located adjacent the lateral periphery of the elongated casing.

20. A hollow fiber dialyzer as in claim 19 wherein there are three passageways having said bundles of fibers and two passageways which do not contain dialysis fibers.

21. A hollow fiber dialyzer having an elongated tubular casing containing partitioning that divides its interior into at least three separate longitudinally-extending passageways, dialyzate flow directing means for receiving dialyzate from an external source and directing it to flow from one casing end to the other through one of the passageways and then back to said one casing end through another of the passageways and so to and fro lengthwise through the other passageways and finally out of the casing, at least two of the passageways each having a longitudinally-extending bundle of elongated hollow blood dialysis fibers extending lengthwise therethrough, and means connected to deliver blood to be dialyzed from an inlet to the fiber ends of each of such bundles at the same end of the casing and to receive the blood from the other ends of the hollow fibers for delivery to an outlet, characterized in that at least one of said passageways does not contain dialysis fibers, and said dialysate flow directing means is adapted to direct dialysate to flow through said at least three passageways so that the direction in which dialysate flows through said at least one of said passageways is opposite the direction in which dialysate flows through at least one of the two passageways having dialysis fibers.

22. A hollow fiber dialyzer having an elongated tubular casing containing partitioning that divides its interior into at least three separate longitudinally-extending passageways, dialysate flow directing means for receiving dialysate from an external source and directing it to flow from one casing end to the other through one of the passageways and then back to said one casing end through another of the passageways and so to and fro lengthwise through the other passageways and finally out of the casing, at least two of the passageways each having a longitudinally-extending bundle of elongated hollow blood dialysis fibers extending lengthwise therethrough, and means connected to deliver blood to be dialyzed from an inlet to the fiber ends of each of such bundles at the same end of the casing and to receive the blood from the other ends of the hollow fibers for delivery to an outlet, characterized in that at least one of said passageways does not contain dialysis fibers, and said dialysate flow directing means is adapted to direct dialysate to flow through said at least three passageways so that the direction in which dialysate flows through said at least one of said passageways is opposite the direction in which dialysate flows through said at least two of the passageways having dialysis fibers.

\* \* \* \* \*